US011727567B2

(12) United States Patent
Regensburger (10) Patent No.: US 11,727,567 B2
(45) Date of Patent: Aug. 15, 2023

(54) METHOD FOR GENERATING SYNTHETIC X-RAY IMAGES, CONTROL UNIT, AND COMPUTER PROGRAM

(71) Applicant: Siemens Healthcare GmbH, Erlangen (DE)

(72) Inventor: Alois Regensburger, Poxdorf (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 18/084,537

(22) Filed: Dec. 19, 2022

(65) Prior Publication Data

US 2023/0196571 A1 Jun. 22, 2023

(30) Foreign Application Priority Data

Dec. 20, 2021 (DE) ...................... 10 2021 214 741.0

(51) Int. Cl.
*G06T 7/00* (2017.01)
*G06V 10/24* (2022.01)
*G06V 10/82* (2022.01)
*G06V 10/74* (2022.01)

(52) U.S. Cl.
CPC ............ *G06T 7/0012* (2013.01); *G06V 10/24* (2022.01); *G06V 10/761* (2022.01); *G06V 10/82* (2022.01); *G06T 2207/10116* (2013.01)

(58) Field of Classification Search
None
See application file for complete search history.

(56) References Cited

U.S. PATENT DOCUMENTS

| | | | |
|---|---|---|---|
| 11,151,703 B2* | 10/2021 | Sargent | G06T 5/50 |
| 2017/0071562 A1* | 3/2017 | Suzuki | A61B 6/5205 |
| 2020/0357148 A1* | 11/2020 | Soons | G06T 7/0012 |
| 2021/0374911 A1* | 12/2021 | Kudo | A61B 6/03 |
| 2022/0293250 A1 | 9/2022 | Kaethner et al. | |

FOREIGN PATENT DOCUMENTS

EP 3447721 A1 2/2019

OTHER PUBLICATIONS

German Decision to Grant for German Application No. 10 2021 214 741.0 decision dated Nov. 17, 2022, with English Translation.
(Continued)

*Primary Examiner* — Samah A Beg
(74) *Attorney, Agent, or Firm* — Lempia Summerfield Katz LLC (57) ABSTRACT

A method for generating synthetic X-ray images is provided. A first neural network is provided to generate at least one synthetic X-ray image having specified quality. A second neural network is provided to ascertain characterizing properties from at least one secondary X-ray image for the first neural network. The first neural network and the second neural network may be trained by primary X-ray images of specified minimum quality. The at least one secondary X-ray image has a lower quality compared to primary X-ray images. The at least one synthetic X-ray image is generated with the aid of the provided characterizing properties by the first neural network. The at least one synthetic X-ray image is improved with regard to quality compared to the at least one secondary X-ray image.

19 Claims, 3 Drawing Sheets

(56) References Cited

OTHER PUBLICATIONS

German Office Action for German Application No. 10 2021 214 741.0 dated Oct. 31, 2022, with English Translation.
Sharma, Sid. "AI Can See Clearly Now: GANs Take the Jitters Out of Video Calls." NVIDIA Blog, Aug. 2020. pp. 1-25.
Wolterink, Jelmer M., et al. "Generative adversarial networks for noise reduction in low-dose CT." IEEE transactions on medical imaging 36.12 (2017): 2536-2545.

* cited by examiner

METHOD FOR GENERATING SYNTHETIC X-RAY IMAGES, CONTROL UNIT, AND COMPUTER PROGRAM

This application claims the benefit of German Patent Application No. 10 2021 214 741.0, filed on Dec. 20, 2021, which is hereby incorporated by reference in its entirety.

BACKGROUND

The present embodiments relate to a method for generating synthetic X-ray images, a control unit for generating synthetic X-ray images, and a corresponding computer program.

Patients are regularly exposed to X-ray beams in the field of interventional radiographs. For this reason, it is frequently deliberated whether and to what extent radiographs are necessary for generating X-ray images. Radiographs are frequently necessary, however, to enable image-assisted therapy management for catheter procedures, orthopedic interventions and/or preparations, or diagnoses. In the case of radiographs or X-ray images, it is frequently a matter of being able to clearly identify a particular object such as a catheter. To provide a high-quality X-ray image, however, radiographs are frequently carried out with a higher exposure to radiation. There is a conflict of interests in this topic in this respect. First, high-quality X-ray images may be necessary to enable optimum treatment, but second, this entails considerable exposure of a person to radiation.

SUMMARY AND DESCRIPTION

The scope of the present invention is defined solely by the appended claims and is not affected to any degree by the statements within this summary.

An important aspect of the present embodiments is based on the finding that in the field of video telephony, a reference image and characteristic perspectives also make video telephony possible at a lower data transfer rate. These findings may be used in a modified manner for producing or generating synthetic X-ray images.

The present embodiments may obviate one or more of the drawbacks or limitations in the related art. For example, a method for generating synthetic X-ray images, with a quality of X-ray images being enhanced, is provided. This is significant since reduced exposure to radiation is to be provided for acquiring X-ray images having a lower quality.

In the present embodiments, a method for generating synthetic X-ray images with the aid of the following method acts is provided. The method serves, for example, to generate synthetic X-ray images of a specified quality. First, in act a), a trained first neural network may be provided to generate at least one synthetic X-ray image of specified quality. Similarly, a trained second neural network may be provided. The second neural network serves, for example, to ascertain characterizing properties from at least one secondary X-ray image and to make these available or provide the characterizing properties to the first neural network. The two neural networks may be trained by primary X-ray images each having a specified minimum quality.

The first neural network may be configured as a Generative Adversarial Network (GAN). A Generative Adversarial Network may include a generating part and a criticizing part. These two parts may compete with each other. For example, the Generative Adversarial Network may include two neural networks. A first subnetwork may be regarded as a generating network, and a second subnetwork may be regarded as a competing or discriminating network. The generating subnetwork may be trained to generate a new improved X-ray image using a template in the form of an X-ray image. The second subnetwork may be configured as a discriminating or criticizing network. This second subnetwork carries out, for example, an assessment of a result of the first subnetwork. For as long as the discriminatory subnetwork does not share the result, the first subnetwork may continue to be trained. This occurs, for example, until the second discriminatory subnetwork shares the result provided by the first subnetwork.

The first neural network, which may be, for example, the totality of the two subnetworks, is based, for example, on a plurality of primary X-ray images having a specified minimum quality. This provides, for example, that the first neural network was trained using the plurality of primary X-ray images having the specified minimum quality. In one embodiment, the first neural network is already trained. The primary X-ray images may be provided beforehand by way of radiographs that have already taken place. The primary X-ray images may correspond to specified situations or reproduce the specified situations. A customary or even increased radiation dose is used to achieve the specified minimum quality. This may provide that the primary X-ray images were generated with a minimum irradiance with regard to the X-ray beams. The primary X-ray images may already exist or may be provided in advance. It is possible, however, to use an X-ray process, which is being carried out anyway, at the same time to provide or generate further primary X-ray images.

Using these high-quality primary X-ray images, the first neural network may be trained to generate an improved, new synthetic X-ray image from a template having reduced quality. The first neural network may thus then be trained, using a secondary X-ray image, which has a lower quality compared to the primary X-ray images, to generate a new improved X-ray image. This new improved X-ray image may be referred to as "secondary plus" or "upgraded secondary image". The new improved X-ray image, which emanates from the secondary X-ray image, may be referred to as a "final" X-ray image or "synthetic" X-ray image. The generated X-ray image may thus be the new X-ray image, the final X-ray image, and/or the synthetic X-ray image.

For this, for example, in a next act b, characterizing properties of the at least one secondary X-ray image are ascertained. Compared to the primary X-ray images, the at least one secondary X-ray image has a lower quality. The at least one secondary X-ray image may be used together with the primary X-ray images during training of the first neural network. From the at least one secondary X-ray image, the first neural network may thus learn to generate a new, final, or synthetic X-ray image, which is improved with regard to quality compared to the at least one secondary X-ray image.

Ascertaining the characterizing properties may be carried out by the second neural network. The second neural network may be regarded as a Deep Neuronal Network (DNN). The second neural network may determine or ascertain the characterizing properties of the at least one secondary X-ray image with the aid of a plurality of slices. The second neural network may make the ascertained characterizing properties available to the first neural network. Using the characterizing properties, which are ascertained by the second neural network, the first neural network may thereby generate the synthetic X-ray image, which has a higher quality than the at least one secondary X-ray image. The quality of the synthetic X-ray image may achieve the level of the primary X-ray images.

In a further act c, at least one synthetic X-ray image may be generated by the first neural network. For this, the first neural network uses the characterizing properties ascertained by the second neural network from the at least one secondary X-ray image.

The first neural network generates the at least one synthetic X-ray image in such a way that the quality of the at least one secondary X-ray image is enhanced. For example, the at least one synthetic X-ray image has a higher quality compared to the at least one secondary X-ray image. A higher quality or a plurality of high-quality synthetic X-ray images may thus be generated from a secondary X-ray image having reduced quality by means of the first neural network and the second neural network. This is very significant since patients are exposed to less radiation in advance. The exposure to radiation may thus be reduced in the case of interventional radiographs without having to accept excessive sacrifices in terms of the quality of the X-ray images in the process.

For example, the characterizing properties from the secondary image may be provided to the first neural network for generating the synthetic X-ray image. Where it is mentioned that the synthetic or final X-ray image is generated by the first neural network using the at least one secondary X-ray image, this may provide that the second neural network ascertains characterizing properties from the at least one secondary X-ray image, transfers the characterizing properties or makes the characterizing properties available to the first neural network, and the first neural network generates the final or synthetic X-ray image using the provided characterizing properties.

The term "quality" may also include a perceived quality. This may include improved identifiability of organs in the X-ray image, an improved, more ergonomic representation, a less noisy X-ray image, sharper textures, and/or improved eye ergonomics. A perceived or subjectively assessed image quality may be addressed in the process. An improved quality may also be objectively defined and/or measured by a resolution, an improved noise level, a brightness, a pixel density, a contrast, and/or a more favorable signal-to-noise ratio (SNR).

Generating the at least one synthetic X-ray image increases the quality of the at least one secondary X-ray image. This may also have an effect on the perceived quality. This may be achieved by the secondary X-ray image with a lower dose and with the two neural networks. For a viewer, the quality of the at least one synthetic X-ray image may look better than the secondary X-ray images. The actual image quality of the secondary X-ray images may be worse, however, than in the case of the primary X-ray images. One aim may be to generate an ergonomic, coherent synthetic X-ray image for the viewer. In detail, the synthetic X-ray images generated by the first neural network may even contain incorrect information or image details, but to a viewer, the synthetic X-ray images still look more coherent and of a better quality than the secondary X-ray images. Apart from the measurable variables such as resolution, brightness, signal-to-noise ratio, noise level, etc., the term "quality" may therefore also be a "perceived image quality", a "subjective image impression" or "image impression for the viewer".

The term quality may, for example, denote image quality, a contrast, a resolution, image noise, and/or a "contrast-to-noise ratio". The term quality may refer to the respective X-ray image. The term "contrast-to-noise ratio" may be regarded as a contrast-to-noise ratio. The contrast-to-noise ratio may be defined as a difference in a signal amplitude between an object and the environment, divided by the background noise. The contrast-to-noise ratio may be used as a measure for determining the image quality. A signal-to-noise ratio may be used in addition or as an alternative to the aspects with respect to the quality. The signal-to-noise ratio is a measure of the technical quality of a useful signal that is embedded in a noise signal. The signal-to-noise ratio may be defined as a ratio of the mean power of the useful signal to the mean noise power of the interfering signal. The quality of the at least one secondary X-ray image may be enhanced by the method. This provides, for example, that one or more synthetic X-ray image(s) that have a higher quality compared to the at least one secondary X-ray image may be generated by the first neural network. A quality of the at least one secondary X-ray image may also be improved thereby. Particular image contents, anatomical structures, and objects may not be identified by the viewer in the X-ray image, or may only be identified with difficulty, in the secondary X-ray image in the original state. These image contents, anatomical structures/objects, may be identified by the viewer, may be more easily identified, or may be visually perceived more easily in the at least one synthetic X-ray image having increased quality.

The characterizing properties in the at least one secondary X-ray image may be outlines, contours, or similar representations to limbs, joints, artificial implants, vessels, vessel branches, tissue boundaries, vessel textures, organs such as heart, kidneys, liver, brain, etc., soft tissues, etc. In addition or as an alternative, artificial items such as catheters, stents, baskets, ribs, vertebra, and/or bones or parts of the items may constitute characterizing properties.

Providing the trained first neural network may also include a training phase of the first neural network. The first neural network may be trained further and improved using further additional primary X-ray images. The first neural network may be trained, for example, using the primary X-ray images. In addition, the characterizing properties of secondary X-ray images may be incorporated in the training. The secondary X-ray images may be derived from the primary X-ray images, as will be illustrated later. Primary X-ray images may be intentionally reduced and/or deteriorated in terms of quality and thus be transferred into further secondary X-ray images. The first neural network may be trained in the training phase using the primary X-ray images and/or using the further secondary X-ray images. It is possible to specify the training phase and/or initiate the training phase based on a quality criterion of the generated at least one synthetic X-ray image.

Using secondary X-ray images, which are generated by intentional deterioration of primary X-ray images, the second neural network may be improved with respect to identification of the characterizing properties and/or the annotation. For this, the second neural network may perform an alignment of the identified characterizing properties from the primary X-ray image with identified characterizing properties from the associated secondary X-ray image. The associated secondary X-ray image may be precisely that X-ray image that is derived from the deterioration of the primary X-ray image and/or results therefrom. Consequently, the second neural network may also be trained and/or improved with respect to the identification of the characterizing properties using the secondary X-ray images that result from the primary X-ray images via a targeted reduction in quality.

Consequently, both the first neural network and the second neural network may be post-trained and/or improved in the case of new primary X-ray images. In one embodiment, further primary X-ray images and the characterizing properties transmitted from the second neural network are transmitted to the first neural network. At the same time, the second neural network may be post-trained using the further secondary X-ray images that are derived from the primary X-ray images (e.g., targeted deterioration of the primary X-ray images).

The training phase serves to train the first neural network and/or the second neural network to the extent that, together, using a "poor" X-ray image (e.g., secondary X-ray image), the first neural network and the second neural network generate an improved synthetic X-ray image having increased quality. Consequently, X-ray images may be improved in terms of perceptibility, quality, or visual ergonomics.

An additional or alternative embodiment provides that an identification rate of the characterizing properties is ascertained. The identification rate may be ascertained by the second neural network or by the first neural network. For example, the quality of the at least one secondary X-ray image is reduced until the identification rate undershoots or attains a specified threshold value. For example, the identification rate may be assessed or compared in relation to an optimum identification rate. The optimum identification rate may result from a primary X-ray image having the specified minimum quality. It is assumed in this case that the characterizing properties in the case of the primary X-ray images are ascertained by the second neural network at a higher identification rate compared to the at least one secondary X-ray image. The second neural network may ascertain the characterizing properties in the case of the primary X-ray images more reliably or with a higher identification rate than in the case of the secondary X-ray images. For example, the quality of the at least one secondary X-ray image may be adjusted to a specified identification rate. The quality of the secondary X-ray images may be reduced further thereby.

The specified threshold value may depend, for example, on the first neural network. In other words, a capacity of the first neural network may influence the specified threshold value. If the first neural network is well trained, the first neural network may still generate a new improved X-ray image that may be adequate, from the at least one secondary X-ray image even in the case of a lower identification rate. This provides that the quality of the secondary X-ray images may be reduced further with the aid of the first neural network. The exposure of people to radiation may thus be reduced further without having to accept serious drawbacks in the generated X-ray images. For example, the first neural network may additionally be trained with the aid of the secondary X-ray images that are reduced further in terms of quality, for generating the at least one synthetic X-ray image. Both neural networks may then be trained to still generate at least one synthetic X-ray image, which attains a specified standard or a specified quality, even in the case of secondary X-ray images having reduced quality.

An additional or alternative embodiment provides that the quality of the at least one secondary X-ray image is established by a specified amount above the threshold value. The first neural network and/or the second neural network may be trained using the at least one secondary X-ray image with regard to ascertaining the characterizing properties and/or with regard to generating the at least one synthetic X-ray image. The secondary X-ray images may also be referred to as low-dose images. Since the secondary X-ray images may be acquired with a lower exposure to radiation, as a rule, the secondary X-ray images have a reduced quality or image quality. The secondary X-ray images may therefore be regarded as low-dose images, and the primary X-ray images may be regarded as high-dose images. Within the context of this embodiment, the second neural network may be "post-trained" with regard to feature identification.

This subsequent training of the second neural network may include an artificial reduction in the quality of the primary X-ray images. The artificial reduction in the primary X-ray images may result in additional further secondary X-ray images. The further secondary X-ray images generated in this way may be derived from the primary X-ray images. This may take place, for example, via algorithms that reduce the image quality of the primary X-ray images in a targeted manner. A further secondary X-ray image may thus be generated. Corresponding algorithms may be used for this. Properties or features in the further secondary X-ray image may be annotated by the second neural network. These identified features may be correlated or aligned with identified features from the associated primary X-ray images.

The features may correspond to the characterizing properties. The characterizing properties may have the same significance as characterizing features. Characterizing properties may be referred to herein, however, since the term "characterizing features" may encompass a legal meaning, which is not addressed here. In this embodiment, the two neural networks may also be trained or post-trained. In the process, it is possible to determine to what extent the quality or the radiation dose may be reduced, so generating the at least one synthetic X-ray image still functions sufficiently well.

For this, the generated or produced at least one synthetic X-ray image may be assessed using a quality value. As long as the quality value of the at least one synthetic X-ray image overshoots a specified limit value, the reduced quality of the secondary X-ray images may be accepted. Optionally, the identification rate may be based on predetermined properties. By way of example, the identification rate may be based on instruments such as catheters, pacemakers, or artificial joints. For example, the quality of the at least one secondary X-ray image may be reduced, and the first neural network and/or the second neural network may be trained iteratively. A further secondary X-ray image having a reduced quality may be provided for this. The first neural network and/or the second neural network may be trained based on this additional secondary X-ray image. The "post-training" already mentioned may likewise be used here. This may be continued until the quality value of the generated synthetic X-ray images attains or undershoots the specified limit value. Consequently, the exposure to radiation during radiography may be reduced even further.

An additional or alternative embodiment provides that the ascertained characterizing properties are transferred to an external control unit by a first data channel having a first latency. In addition or alternatively, the plurality of primary X-ray images having the specified minimum quality, information derived from the primary X-ray images, and/or the first neural network may be transferred to the external control unit by a second channel having a lower second latency for an external implementation of the method. The first neural network may be transferred in the form of a data packet or dataset. By way of example, a scaling factor or zoom factor may be assigned to the primary X-ray image and be transferred via the second data channel. Similarly, a relevant region of the primary X-ray images may be defined for generating the synthetic X-ray images. This information may be regarded as information derived from the primary X-ray images. The external execution may be regarded as distance work or as a remote execution. The latency or latency time of the second data channel may be reduced in comparison with the first latency time of the first data channel. The second latency may be between 10 and 100 milliseconds. For example, the second latency may be less than 40 milliseconds or less than 10 milliseconds. External training of the two neural networks may be optimally carried out thereby. The first neural network may receive the primary X-ray images via the second data channel, while the second neural network may receive the characterizing properties via the first data channel. The respective neural networks may have appropriate interfaces for this. A separate interface may be provided for each data channel. The method for generating the synthetic X-ray images or training the two neural networks may thereby take place independently of apparatuses that generate synthetic X-ray images. By way of example, an external computer unit or external processing unit may include these two neural networks and thus carry out the method.

An additional or alternative embodiment provides that the second neural network is trained using the at least one secondary X-ray image and/or using a secondary X-ray image derived from the at least one primary X-ray image. The second neural network may be improved or trained to identify the characterizing properties thereby. The second neural network may thus be trained further in a targeted manner. For example, this additional training may be dependent on an identification rate with regard to the characterizing properties. The additional training of the second neural network may be based on specified characterizing properties. The at least one primary X-ray image may be deteriorated in a targeted manner in relation to image quality. Appropriate methods or algorithms may be used for this. One or more secondary X-ray image(s) may be derived thereby from one primary X-ray image, respectively, and these may be referred to as "deteriorated primary X-ray images". These derived secondary X-ray images may be assigned to the corresponding primary X-ray images.

The second neural network may ascertain characterizing properties from the at least one primary X-ray image and the associated derived secondary X-ray images respectively. The second neural network may compare or mutually align the different characterizing properties for training. For example, the characterizing properties identified by the second neural network or other algorithms in the primary X-ray image may be annotated in the derived secondary images at the corresponding locations. These annotated derived secondary X-ray images may be used for "post-training" of the second neural network.

In addition or alternatively, the specified characterizing properties may be changed or modified in a targeted manner to increase the identification rate with respect to the specified characterizing properties by training the second neural network. By way of example, the second neural network may be provided with a large number of X-ray images relating to different hip joints or implants for training. Consequently, the second neural network may be improved with respect to the identification rate for artificial hip joints or implants. The second neural network may be improved with regard to its ability to identify artificial hip joints by this post-training. Regarding other features such as pacemakers, vertebra, ribs, etc., an analog post-training may take place. This training or post-training may be used analogously for the first neural network. In one embodiment, additional primary X-ray images and further secondary X-ray images derived from the additional primary X-ray images are used for training. These further secondary X-ray images may be generated by a reduction in the image quality of the primary X-ray images. Consequently, the reliability or efficiency of the two neural networks and of the method for generating improved X-ray images may be enhanced further.

An additional or alternative embodiment provides that synthetic X-ray images of specified quality may be generated. For this, a separate quality criterion may be ascertained for each generated synthetic X-ray image. The quality criterion may be expressed in the form of the quality value. The quality criterion may be, for example, a resolution or the identification rate. Similarly, a contrast, a contrast-to-noise ratio, a consistency check having the underlying secondary X-ray images, and/or a signal-to-noise ratio may be valid as a quality criterion. For reasons of simplicity, the resolution or a noise level will be regarded as the quality criterion below. A separate resolution may be determined as the quality criterion thereby for each generated synthetic X-ray image. As a function of the respective quality criterion, in this case, the resolution, the first neural network may be trained with the aid of additional primary X-ray images of specified minimum quality and/or using secondary X-ray images derived from the additional primary X-ray images. The second neural network may ascertain the characterizing properties from secondary and/or primary X-ray images and provide them to the first neural network for training. The characterizing properties that are ascertained from the primary X-ray images may be aligned with the characterizing properties that are ascertained from the associated secondary X-ray images. Consequently, an identification rate relating to the characterizing properties may be enhanced by the second neural network.

The additional primary and/or secondary X-ray images may be modified as a function of the quality criterion. The quality criterion may refer to a segment in the X-ray image that is of interest. If, for example, a hip joint is to be examined, then as a quality criterion, a resolution or a noise level in that field of view of the X-ray image may be addressed, which shows the artificial hip joint. The quality criterion may thus refer to a physical region with respect to the characterizing properties.

Training may take place as a function of the respective separate quality criterion with the aid of this embodiment. The additional primary and/or secondary X-ray images may be modified based on the respective quality criterion. Consequently, the two neural networks may be trained in a targeted manner to the respective quality criterion or to a quality that is to be attained for the generated synthetic X-ray images. It is possible to match the additional primary and/or secondary X-ray images to a new specified situation. As a rule, the first and/or second neural network may be trained or adjusted with regard to new situations. A reliability and/or efficiency of the method may thus be increased further.

The quality criterion may be expressed by a quantitative quality value such as an identification rate, a resolution, a signal-to-noise ratio, or a consistency in relation to a specified image. The quality criterion may include a comparison of the quantitative quality value with a specified limit value or threshold value. A synthetic X-ray image may thus be subjected to quality control. If the quantitative quality value overshoots the specified limit value, the synthetic X-ray image may thus be graded satisfactory. If the quality value undershoots the specified limit value, however, this may be cause for further training of the first neural network and/or the second neural network. For this, further primary and/or secondary X-ray images may be used for training.

For example, in the case of a control, the aim may be to reduce the quality of the secondary X-ray images until the quality criterion is not met for the first time; the quality value undershoots the specified limit value for the first time, therefore. For this, the quality criterion may be checked iteratively. A quality value determined in each iterative step may be compared with the specified limit value respectively in order to assess the quality criterion. In this case, a quality of the secondary X-ray images has been determined, which is only just adequate. This approach may be logically transferred and applied to all embodiments with respect to the quality criterion or of the quality value. This may result in much reduced exposure to radiation.

An additional or alternative embodiment provides that for training or for checking the method, the second neural network ascertains characterizing properties using at least one additional primary X-ray image and provides, transfers, or makes the ascertained characterizing properties available to the first neural network. The first neural network may generate an additional synthetic X-ray image using these provided characterizing properties. The additional synthetic X-ray image may be compared and/or aligned with the at least one additional (e.g., new) primary X-ray image. The second neural network may be improved thereby with regard to feature identification (e.g., identification of the characterizing properties; therefore, using new primary X-ray images). This improvement may result in an improvement of the quality of the synthetic X-ray image. If the quality of the synthetic X-ray image is above an established limit, the quality of the secondary X-ray images may be artificially reduced and this embodiment may be carried out again. The quality of the synthetic X-ray images may thus be increased, and/or a lower quality in the case of the secondary X-ray images may suffice to maintain a specified quality limit in the case of the synthetic X-ray images using additional primary X-ray images.

An additional or alternative embodiment provides that training the first neural network and/or the second neural network is initiated by additional primary X-ray images of specified minimum quality as a function of defined criteria. The method may thus be transferred based on the defined criteria into a training phase again. The defined criteria or a defined criterion may be an established duration, a changed process when generating the primary or secondary X-ray images, detection of a catheter robot, a reduction in the identification rate with respect to the characterizing properties, a detected movement in a sequence of a plurality of X-ray images, a quality criterion, and/or change in the respective X-ray image. In addition or alternatively, a defined criterion may be a camera-based, captured movement of a patient in the primary or secondary X-ray image, and/or a change of attenuation values in the primary or secondary X-ray image by a specified minimum amount. All circumstances that may influence the method for generating high-quality X-ray images from the secondary X-ray images may be defined as criteria. The first neural network and/or the second neural network may be transferred into the training phase again based on these criteria. It is thus possible to react to changed circumstances flexibly, and the two neural networks may be adjusted to the changed circumstances by way of the renewed training.

An additional or alternative embodiment provides that the specified criterion is defined as an established duration, a change in an acquisition method of the at least one secondary X-ray image, a detected movement in the at least one secondary X-ray image, a consistency between the generated (e.g., synthetic) X-ray image and the associated secondary X-ray image, and/or a signal relating to a newly identified object in the at least one secondary X-ray image. Even when patients are exhorted to remain as still as possible during radiography, movements may nevertheless be identified in the respective X-ray image owing to a respiratory movement or a heartbeat. In the case of a detected movement, the second neural network may be trained in a targeted manner to predict and/or parameterize movement of the characterizing properties. Similarly, the first neural network may be trained with regard to movements with respect to the characterizing properties. By way of example, in the case of a heartbeat, a catheter or a stent may be subjected to a movement in a sequence of X-ray images. The first neural network and/or the second neural network may be trained in a targeted manner to predict or parameterize an effect of such movements on the characterizing properties in the respective X-ray image. Since a lot of movements of this kind, such as breathing or a heartbeat, are cyclical, a position of the properties to be characterized in the respective X-ray image may be predicted. Consequently, positions of the characterizing properties may be predicted and/or identified better in the respective X-ray images. The characterizing properties include, for example, objects that are especially of interest, such as catheters, stents, artificial joints, pacemakers, and/or further implants, for example.

The consistency may be determined by a comparison of the synthetic X-ray image with the secondary X-ray image. By way of example, the extent to which content-related structures or high-contrast objects match in the two X-ray images may be determined for this purpose. This may take place using a correlation value. A similarity between the secondary and the synthetic X-ray image may be expressed by way of a correlation value and be compared with a specified threshold value. The consistency may thus be evaluated. Alternatively, the quality of the synthetic X-ray image may be deteriorated again to reset a lower acquisition dose, and the deteriorated X-ray image may be compared with the secondary X-ray image.

An additional or alternative embodiment provides that a first region and a second region may be established in the case of the at least one secondary X-ray image. These regions may be regarded as segments of the at least one secondary X-ray image. The quality in the second region may be at least partially lower or at least partially reduced in comparison with the first region. With the aid of the first neural network, a quality in the second region may be increased using identified characterizing properties within the first region. This may take place, for example, with the aid of an extrapolation. Since the second region has a reduced quality or image quality compared to the first region, for the preceding radiography, this provides that a required radiation dose may be reduced further. A higher radiation dose may thus be limited to the first region. Using the characterizing properties within the first region, a higher quality may still also be attained in the second region via the first neural network.

For example, this embodiment may be applied solely to the second region. A quality of the secondary X-ray images may be set such that it is adequate in the first segment. This embodiment of the invention may then be applied in the second segment to improve the perceived quality there. By way of example, the first segment may be important for the success of a treatment, while the second segment shows only less relevant adjacent regions that may nevertheless be represented with appealing perceived quality.

An additional or alternative embodiment provides that the quality in the second region is reduced by a beam filter, and/or the quality solely in the second region is increased by the first neural network.

For example, the segments may be established by a source-side radiography filter, with more radiation being let through by the filter in the first segment than in the second segment. By applying a method of the present embodiments in the second segment, the perceived quality may be increased there despite a reduced radiation dose.

An additional or alternative embodiment provides that using a plurality of secondary X-ray images, the associated characterizing properties respectively are detected by the second neural network, and a movement of the characterizing properties and/or regions of the X-ray images adjoining the characterizing properties is parameterized by the first neural network. The second neural network may thus detect one position respectively of the characterizing properties in the respective secondary X-ray images, and the first neural network may ascertain therefrom a movement of the characterizing properties using these different detected positions of the characterizing properties. This movement may be parameterized by the first neural network. The first neural network and the second neural networks may thus cooperate for movement identification or parameterization. This embodiment may be applied accordingly in the respective X-ray image to the first region and/or second region. A movement in the first region may thus be identified, and the movement identified in the first region may be transformed or converted (e.g., by extrapolating) to the second region of the secondary X-ray image. By way of example, a catheter in the secondary X-ray image may be arranged in both the first and in the second regions. In this case, it is sufficient if the movement of the catheter is identified in one of these two regions and parameterized. The movement of the catheter in the other region may thus be predicted accordingly. Movements may thus also be taken into account by the first neural network and/or the second neural network when generating the synthetic X-ray images. This may at best render additional radiographs superfluous, and this may spare the patient from unnecessary exposure to radiation.

An additional or alternative embodiment provides that for providing and/or training the first neural network, as an alternative or in addition to the primary X-ray images, further primary images are provided from a second modality different to radiography as the first modality. The first modality may refer to X-ray images that were generated by a corresponding radiography device. The second modality may refer to images that were generated by another method or another apparatus.

The second modality may refer by way of example to an electromagnetic tracking system, fiber optic shape sensing, ultrasound technology, MRT sequence images, etc. The second modality may thus include a plurality of different modalities or sources for the respective images. The primary X-ray images may thus originate from different sources. It is possible that all primary images originate from the second modality. In this case, the first neural network may be trained solely using images that are not X-ray images. In one embodiment, the first neural network is trained with the aid of X-ray images from the first modality and additionally with the aid of primary images from the second modality. Each image may be assigned to one modality.

The first neural network may be trained based on the primary X-ray images. A third neural network may obtain characterizing properties from the secondary images of the second modality. The third neural network may have a similar structure to the second neural network. The second neural network and the third neural network may correlate. The second neural network and the third neural network may differ based on the data sources used. While the second neural network ascertains characterizing properties from X-ray images, in the third neural network, this occurs using further, different images or data sources. The results of the third neural network may be converted for the second neural network, and vice versa. A coordinate transformation may be used for this.

The third neural network has, for example, the task of identifying the characteristic features (e.g., position and locations of landmarks) in the images/data of the second modality. The third neural network may also have already been trained in advance. The locations and/or coordinates of characteristic features from the second modality detected by the third neural network may be transferred using coordinate transformation or a known registering into the coordinates of the X-ray image. As in the previous exemplary embodiments, the first neural network may then be used to generate a new improved X-ray image based on the coordinates and types of characterizing features.

Similarly, as an alternative or in addition, the secondary X-ray images may originate from the first modality or the second modality. A first portion of the characterizing properties may thereby be detected from the secondary images of the first modality, and a second portion of the characterizing properties may be obtained from images of the second modality. The second neural network may thereby capture or detect the characterizing properties from images from different modalities. Consequently, the reliability or robustness of the identification of characterizing properties may be increased. A totality of the identified characterizing properties may be supplied to the first neural network to generate therefrom at least one further additional X-ray image having improved quality. The database for the two neural networks may be improved based on the images of the second modality. In the best case, a further reduction in quality with respect to the at least one secondary X-ray image may be achieved thereby. This corresponds to a reduction in the exposure to radiation during a radiography procedure. For example, chronically ill people who are frequently dependent on radiographs or children may thus benefit from significantly reduced exposure to radiation. At the same time, these people have to accept slight or hardly any sacrifices in the quality of treatment.

An additional or alternative embodiment provides that the second neural network is trained using secondary X-ray images from the first modality and secondary images from the second modality. The advantages, examples, and features with respect to the above-mentioned embodiment apply logically and analogously in this case.

An additional or alternative embodiment provides that a first portion of the characterizing properties is obtained by the second neural network from the at least one secondary X-ray image of the first modality and a second portion of the characterizing properties from the secondary images of the second modality. The first neural network may generate at least one new X-ray image using a totality of the characterizing properties from the first and second portions. Consequently, the characterizing properties may be more reliably identified by the second neural network. The identification rate with respect to the characterizing properties may thus be increased.

An additional or alternative embodiment provides that the quality of the at least one secondary X-ray image is reduced, and based on the ascertained quality criterion relating to the at least one generated synthetic X-ray image, the first neural network is trained as a function of the quality criterion using additional primary X-ray images from the first modality and/or additional primary images from the second modality having a specified minimum quality respectively. The features of the previously mentioned embodiment with respect to the separate quality criterion may be applied logically and analogously to this embodiment. This provides that the examples and features cited there may be transferred logically and analogously to this embodiment. The first neural network may thus be trained again or iteratively if the quality criterion undershoots a specified limit value. These two embodiments may additionally include training of the second neural network.

In addition, the quality of the secondary X-ray image may be incrementally reduced during the course of control. Quality control may take place in each step by way of a comparison of the quality value with the specified limit value. Iterative quality control may thus be carried out. This control may be continued or may include so many steps until the specified limit value is undershot or attained for the first time. When the specified limit value is undershot for the first time, the quality of the secondary X-ray images is reduced to this extent but is still adequate for the first neural network to generate therefrom the final or synthetic X-ray image having specified minimum quality. A potential of the method or the control unit having the first neural network and the second neural network is exploited to the maximum by this control.

The second neural network may be trained, as a function of the quality criterion, using additional secondary X-ray images from the first modality and secondary images from the second modality. Training may also include retroactive training. For example, further secondary X-ray images may be obtained for post-training via a reduction in the quality of primary X-ray images. The characteristic properties may first be detected in the primary X-ray images by the second neural network. These properties may be used in the further secondary X-ray image (e.g., deteriorated primary X-ray image) as an annotation during additional training of the second neural network. The aspects around the derived secondary X-ray images may be transferred logically and analogously to the images from the second modality.

The quality criterion may refer to an identification rate of the characterizing properties. Similarly, the quality criterion may refer to a resolution that is assigned to a particular field of view. In one embodiment, a resolution in the region of the characterizing properties is considered. As a rule, a higher resolution is desired there than in other fields of view, which are less relevant to patient treatment. These two neural networks may be significantly improved by training the first neural network or the second neural network using X-ray images from the first modality and images from the second modality. This is due, for example, to the fact that the two neural networks are trained using different data sources. The method for generating improved X-ray images may thus be optimized further.

A second aspect of the present embodiments relates to a control unit for generating synthetic X-ray images. The control unit has a first neural network, which may include two competing networks. The first neural network may have been trained in advance. The first neural network is configured, for example, to produce or generate at least one synthetic X-ray image of specified quality. The first neural network may be trained based on a plurality of primary X-ray images each having a specified minimum quality and/or information derived therefrom. The first neural network may be configured, for example, as a Generative Adversarial Network. The control unit also has a second neural network. The second neural network may be configured as a Deep Neuronal Network. The second neural network may be configured to ascertain characterizing properties from at least one secondary X-ray image. The characterizing properties may be extracted from the primary X-ray images in a training phase to improve the second neural network. In an application phase, the second neural network ascertains the characterizing properties using, for example, the at least one secondary X-ray image and makes the characterizing properties available to the first neural network. Compared to the primary X-ray images, the secondary X-ray image has a lower quality. In addition, the first neural network is configured to generate the at least one synthetic X-ray image using the characterizing properties ascertained by the second neural network. In one embodiment, the quality of the at least one secondary X-ray image is enhanced in the process. The two neural networks may be trained or post-trained with the aid of additional primary X-ray images each having a specified minimum quality. The examples, advantages, and embodiments cited in the connection with the first aspect apply logically and analogously to the second aspect.

A further embodiment provides a control unit in which the second neural network is adapted to ascertain, vertebra, fingers, hips, joints, and/or a pelvis as characterizing properties from the at least one secondary X-ray image. The second neural network may be trained or adapted to identify relevant objects in the at least one secondary X-ray image. These relevant objects represent the characterizing properties. These include bones, vertebra, fingers, hips, artificial joints, catheters, stents, and/or artificial implants. Similarly, internal organs such as the heart, lungs, kidneys, and so on may be addressed as relevant objects or characterizing properties.

A third aspect of the present embodiments relates to a computer program. When the computer program or the program is executed by a computer, this causes a computer to carry out the method for generating synthetic X-ray images. This provides that the computer program may include commands that, when the program is executed by a computer, cause the computer to carry out one of the embodiments.

A fourth aspect relates to an electronically readable data carrier having electronically readable control information stored thereon. The data carrier may include the computer program and be configured such that the computer program carries out each embodiment of the described method when the data carrier is used in a control unit or a computer.

The computer program may likewise include a storage medium or a computer-readable storage medium (e.g., a non-transitory computer-readable storage medium) and a computer-readable data carrier. The computer program may be stored on the storage medium or the computer-readable data carrier. The computer program may be transferred with the aid of a data carrier signal to the storage medium and be stored there.

The control unit may include a computer program and/or a data carrier, which contain commands that cause each embodiment of the method to be carried out. The computer program may be stored on a computer-readable medium.

The features, embodiments and their advantages presented in connection with the method for generating synthetic X-ray images according to the first aspect of the present embodiments apply accordingly to the control unit according to the second aspect of the present embodiments, to the computer program according to the third aspect, to the data carrier according to the fourth aspect, and vice versa, respectively. Features of the method may thus be interpreted as features of the apparatus, and vice versa.

The control unit may have a processor facility that is configured to carry out an embodiment of a method. The processor facility may have for this purpose at least one microprocessor, at least one microcontroller, at least one Field Programmable Gate Array (FPGA), at least one Digital signal Processor (DSP), and/or a neural network for this. Further, the processor facility may have program code that is configured to carry out the embodiment of the method when executed by the processor facility. The program code may be stored in a data memory of the processor facility. The control unit may include an internal or external memory unit. The external memory unit may be configured as a Cloud unit.

BRIEF DESCRIPTION OF THE DRAWINGS

The invention will now be illustrated in more detail using exemplary drawings. These drawings represent merely exemplary embodiments of the invention. The drawings do not limit the scope of the invention and serve merely to facilitate understanding of the invention. For example, all features addressed in the drawings may be extracted and linked to the embodiments already mentioned.

DETAILED DESCRIPTION

Figure 1:
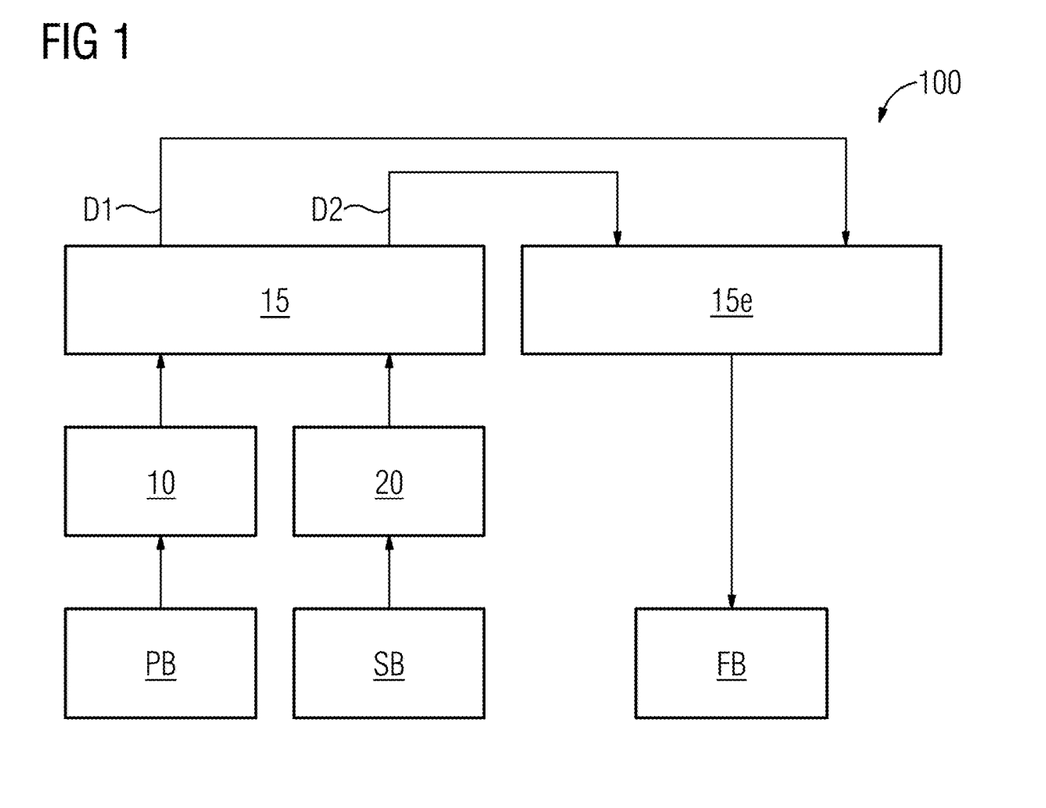
FIG. 1 shows an exemplary overview of an external control unit for generating synthetic X-ray images.

FIG. 1 shows by way of example a control unit 100. The control unit 100 may include, for example, a first neural network 10 and a second neural network 20. The first neural network 10 may be trained using a plurality of primary images PB. The second neural network 20 may be trained using at least one secondary image SB. In FIG. 1, data of primary or secondary X-ray images collected by the first neural network 10 and the second neural network 20 is transferred to an external control unit 15e via a computing unit 15. The secondary X-ray images SB may be transferred via a first data channel D1, and the primary X-ray images PB and/or the first neural network 10 may be transferred to an external computing unit 15e via a second data channel D2. The external computing unit 15e may likewise have the first neural network 10 or the second neural network 20 or access the first neural network 10 and the second neural network 20.

Figure 4:
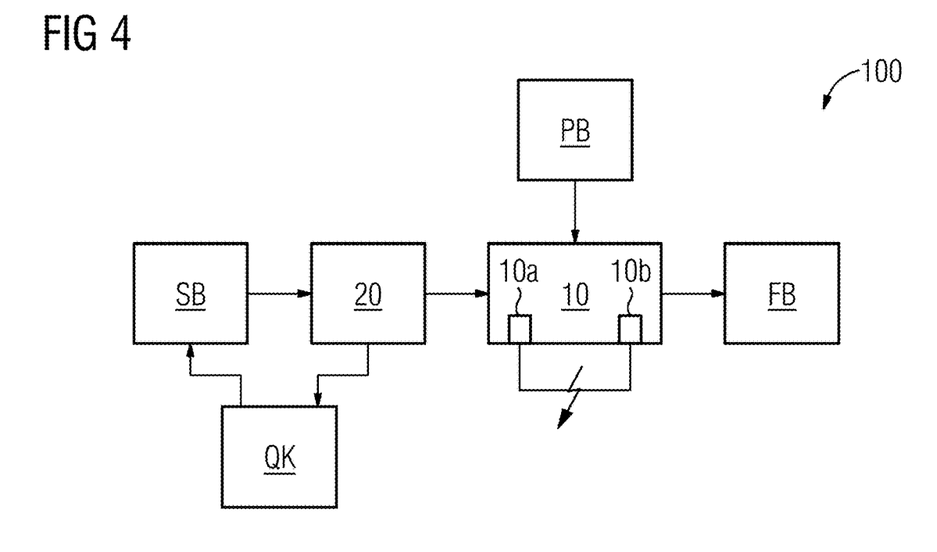
FIG. 4 shows a schematic overview of an exemplary control with respect to quality of the secondary images.

The first neural network 10 may have two neural networks that compete with each other. The first neural network 10 may be configured, for example, as a Generative Adversarial Network. A first subnetwork 10a may be configured as a generating network, while a second subnetwork 10b may be network competing therewith. FIG. 4 indicates, by way of example, with the aid of a flash between the first subnetwork 10a and the second subnetwork 10b, competition between these two networks. The first neural network 10 is trained to generate a synthetic X-ray image FB based on characterizing properties and the primary X-ray images PB. The synthetic X-ray image FB may also be referred to as a final X-ray image FB. For this, the first neural network 10 accesses the characterizing properties, which are captured by the second neural network 20. The first neural network 10 may generate the synthetic X-ray image FB with the aid of the primary images PB and the characterizing properties. The control unit 100 or the first neural network 10 is trained such that the synthetic X-ray image FB has a higher quality than the secondary X-ray image SB.

Figure 2:
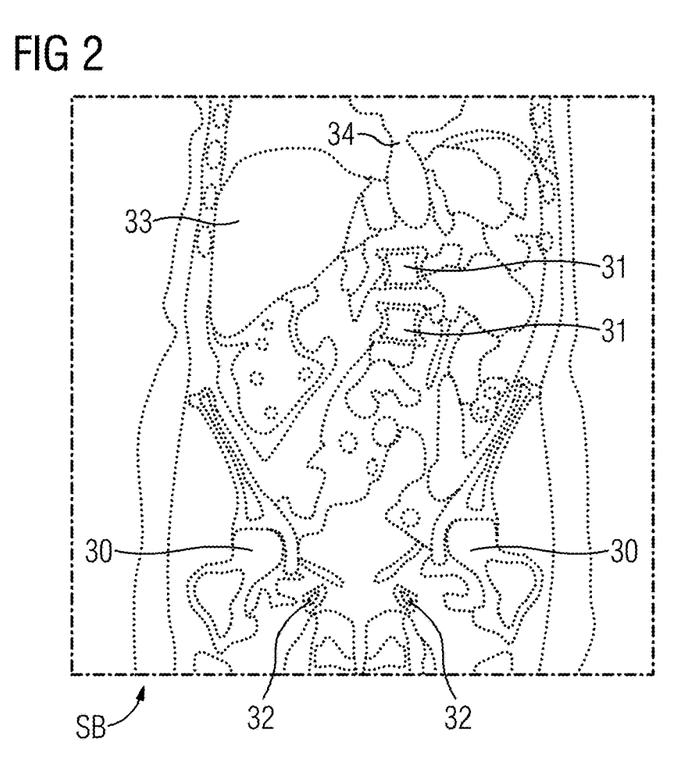
FIG. 2 shows an exemplary representation of a secondary X-ray image.
Figure 3:
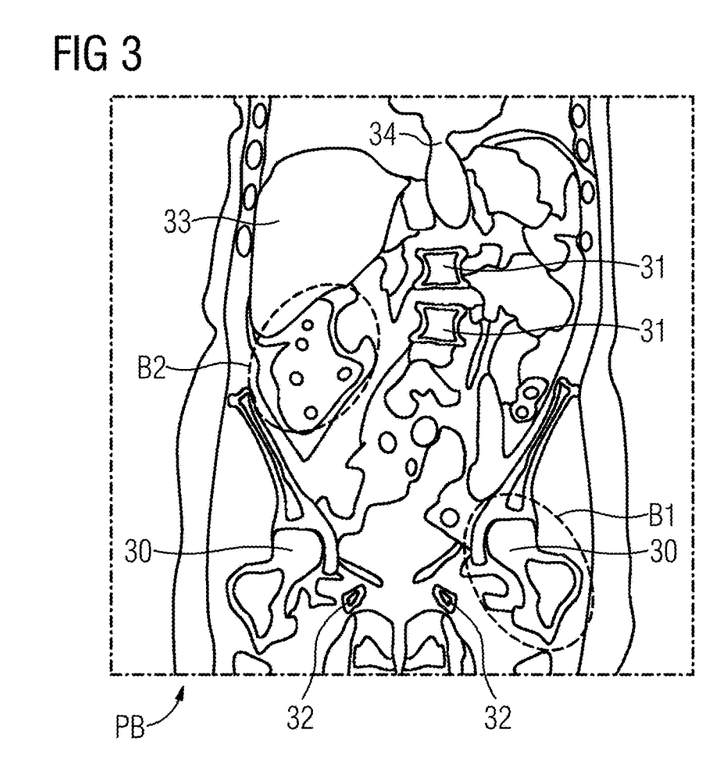
FIG. 3 shows an exemplary representation of a primary X-ray image.

FIG. 2 and FIG. 3 show similar X-ray images, respectively. FIG. 2 shows a secondary X-ray image SB, while FIG. 3 shows the associated primary X-ray image PB. It is possible to clearly see that the primary X-ray image PB is of a higher quality than the secondary X-ray image SB. In this case, the primary X-ray image PB has a higher resolution compared to the secondary X-ray image SB. In FIG. 2, the secondary X-ray image SB is slightly more pixelated than the associated primary X-ray image PB in FIG. 3. Nevertheless, the second neural network 20 may identify characterizing properties 30 to 34 using the secondary X-ray image SB. The characterizing properties may include, by way of example, a hip bone 30 or hips 30, a plurality of vertebra 31, a pelvis 32, and/or organs such as a liver 33. A cervical vertebra 34 may also be considered as a relevant object, as characterizing properties 30 to 34, therefore. An actual embodiment of the characterizing properties 30 to 34 may be dependent, for example, on a treatment or a patient.

The first neural network 10 may receive the characterizing properties 30 to 34 from the second neural network 20. Since the first neural network 10 is trained with the aid of the primary X-ray images PB, it is capable of generating a synthetic, further, or final X-ray image FB from the characterizing properties 30 to 34. Compared to the secondary X-ray image SB, the synthetic X-ray image FB has an enhanced quality. By way of example, a resolution in the region of the characterizing properties 30 to 34 may be increased. Low-dose images (e.g., secondary X-ray images SB) may be used thereby during radiography, and nevertheless, an image quality similar to that in the case of high-dose X-ray images (e.g., primary X-ray images PB) may be achieved.

The first neural network 10 or the two competing neural subnetworks 10a and 10b may qualitatively enhance the at least one secondary X-ray image SB. The focus of the quality enhancement is, for example, the characterizing properties 30 to 34. Primarily, it may be a matter of being able to clearly identify relevant objects such as a catheter. Similarly, the synthetic X-ray image FB may be generated with a realistic soft tissue background from the secondary X-ray image SB with the aid of the first neural network 10 and the second neural network 20. Consequently, objects such as bones or instruments may be identified more clearly, and the synthetic X-ray image FB may appear more natural.

When generating the synthetic X-ray image FB, it is a matter, for example, of representing contours and/or positions of the relevant objects (e.g., characterizing properties in the image) correctly with respect to position and form. It is not inevitably a matter of representing intricate details within these relevant objects exactly and correctly, however. By way of example, a soft tissue background would be of no interest for an orthopedic procedure. While it may be more appealing to generate a virtual soft tissue background when generating the synthetic X-ray image FB, the primary focus is displaying an anatomy of a patient correctly. It is important that the anatomy of the correct patient is displayed, and that an anatomy of a different patient is not incorporated in the synthetic X-ray image FB. This may be provided, for example, by additional training of the first neural network 10 in a training phase.

FIG. 4 shows by way of example a training phase for the second neural network of the control unit 100. The first neural network 10 acquires the primary X-ray images PB as input data. The first neural network may be configured as a Generative Adversarial Network, which has two neural networks that compete with each other. The two subnetworks 10a and 10b are represented as competing neural subnetworks in FIG. 4, and this is symbolized by the flash. Using the secondary X-ray image SB, the second neural network 20 identifies a plurality of characterizing properties 30 to 34. A result of this identification of properties or features may be supplied to quality control QK. Quality control or the quality criterion QK may include a comparison of an identification rate with a specified threshold value. If the quality criterion QK reveals that the identification rate is above the specified threshold value, the quality of the secondary X-ray images SB may be reduced further. This reconstructs the situation as to how the secondary X-ray images SB would look if the secondary X-ray images SB were to have been acquired with a lower radiation dose. The second neural network 20 may thus then be trained to still identify the characterizing properties 30 to 34 or relevant objects from the secondary image SB even if the characterizing properties 30 to 34 or relevant objects from the secondary image SB have a lower quality.

In an optional test phase, it is possible to ascertain with which reduced quality the object identification or identification of the characterizing properties (e.g., feature identification) still functions adequately. Particular features or objects may be selected in this case. The quality criterion QK may be specially directed to specified objects or characterizing properties 30 to 34. These relevant objects may be by way of example instruments such as stents, catheters, or other high-contrast structures.

In one embodiment, the primary X-ray images PB having a specified minimum quality are used during a training phase of the first neural network 10. This training phase may be carried out repeatedly to update changes to a background anatomy. Particular criteria in which the method switches back to a training phase may be defined. This criteria may include an established duration, a change in a treatment of the patient, a detected change of instrument, a captured signal of a catheter robot, a reduced identification rate with respect to a relevant object of a detected movement or change in the primary or secondary X-ray image, a camera-based captured movement of the patient, and/or a change in the attenuation rate in the X-ray image. Depending on the situation, the training phase for the first neural network 10 and/or the second neural network 20 may be carried out again if one of the criteria occurs.

The first neural network 10 and/or the second neural network 20 may be trained, for example, on the external computing unit 15e. Training of the two neural networks is thus particularly well suited to a "Remote Use Case". The speed of the data transfer section may be taken into account in this case. In one embodiment, the second data channel D2, which has a lower latency time compared to the first data channel D1, is used with respect to the primary X-ray images PB. FIG. 3 indicates a first region B1 and a second region B2. The first neural network 10 may increase a quality in the second region B2 (e.g., using relevant objects and/or characterizing properties 30 to 34 in the first region B1). For example, the first neural network 10 may increase the quality in the second region (e.g., by extrapolation) based on the characterizing properties 30 to 34 in the first region B1.

This may also apply to movements that are identified in the first region B1 and may have an effect on the second region B2. By way of example, a movement identified in the first region B1 may be parameterized, and with the aid of this parameterization, effects in the second region B2 may be ascertained and be displayed in the synthetic X-ray image FB accordingly. It may thus be sufficient if minimum quality specified in the primary X-ray images PB refers only to particular specified regions.

Figure 5:
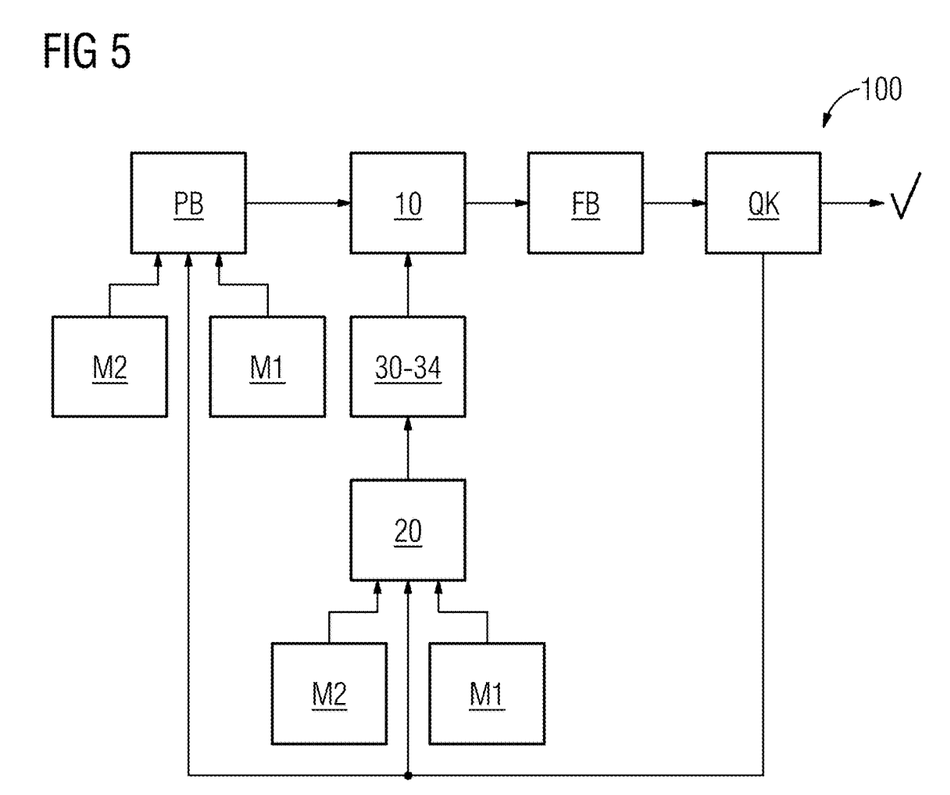
FIG. 5 shows an exemplary overview of a control for post-training two neural networks based on a quality criterion.

FIG. 5 indicates by way of example one possible method for control of the first neural network 10 and/or of the second neural network 20. While FIG. 5 specifically shows control of the second neural network 20, the control represented therein can be analogously transferred to the first neural network 10. The control may even be applied to the first neural network 10 and the second neural network 20 simultaneously.

The first neural network 10 is trained with the aid of the primary X-ray images PB. The first neural network 10 is then trained to generate the synthetic X-ray image FB using the characterizing properties 30 to 34, which are detected by the second neural network 20. The synthetic X-ray image FB has a higher quality compared to the secondary X-ray image SB. This may be by way of example a higher resolution. The synthetic X-ray image FB may be assessed with the aid of the quality criterion. For this, a quality value with respect to the synthetic X-ray image FB may be compared with a specified limit value. Once the specified quality limit value has been attained, the synthetic X-ray image FB may be shared.

If the specified quality limit value is undershot, a further training phase may follow. This further training phase may relate to both the first neural network 10 and the second neural network 20. Additional X-ray images from a first modality M1 may be used in this case. These additional X-ray images may relate to both the primary X-ray images PB and the secondary X-ray images SB. Alternatively or in addition, further images from the second modality M2 may be supplied to the respective neural networks for the purpose of training. The second modality M2 may relate to imaging methods that are not based on X-ray beams. By way of example, MRI images or photographs may be used as additional images of the second modality M2 for training the first neural network 10 and/or the second neural network 20. Depending on which quality criterion QK is being used and to what extent a set quality target is missed, it is possible to decide whether only the first neural network 10, only the second neural network 20, or both the first neural network 10 and the second neural network 20 are supplied to a renewed training phase.

The control loop shown in FIG. 5 may be carried out until the generated synthetic X-ray images FB satisfy the set quality requirements. The second modality M2 may refer to an electromagnetic tracking system for a catheter, to fiber optic shape sensing, to ultrasound, and and/or to fast MR sequences. A hybrid data structure may be created for training the respective neural networks by using X-ray images and images from different modalities. Some of the relevant objects or characterizing properties 30 to 34 respectively may be captured or identified from each modality. A high-quality synthetic X-ray image FB may be created with the aid of the totality of the identified characterizing properties 30 to 34 from the first modality M1 and the second modality M2 by the second neural network 20 with the aid of the first neural network 10.

The method and the associated embodiments thus make it possible to increase the robustness of the identification of relevant objects and create the possibility of generating the secondary X-ray images SB with less exposure to radiation. This applies, for example, to the case where particular properties have already been identified using the data from the second modality. Synthetic X-ray images FB may be created thereby, which may represent a realistic anatomical background. While, in principle, this may also be achieved with corresponding high-dose X-ray images, the present embodiments make it possible to generate high-dose X-ray images without patients having to be exposed to this increased level of radiation. A synthetic X-ray image FB of adequate quality may nevertheless be created with the aid of the present embodiments and the associated embodiments using X-ray images from the first modality M1 or images from the second modality M2 that were generated by a low exposure to radiation. Unpleasant side effects may be reduced thereby.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for generating synthetic X-ray images, the method comprising:
providing a trained first neural network for generating at least one synthetic X-ray image of specified quality, and a trained second neural network for providing characterizing properties from at least one secondary X-ray image for the first neural network, wherein the first neural network and the second neural network are trainable by primary X-ray images each having a specified minimum quality;
ascertaining the characterizing properties using the at least one secondary X-ray image that has a lower quality compared to the primary X-ray images, by the second neural network; and
generating the at least one synthetic X-ray image by the first neural network using the characterizing properties provided by the second neural network, the at least one synthetic X-ray image being improved with respect to quality compared to the at least one secondary X-ray image.

2. The method of claim 1, further comprising:
ascertaining an identification rate of the characterizing properties by the second neural network; and
reducing the quality of the at least one secondary X-ray image until the identification rate undershoots a specified threshold value.

3. The method of claim 2, wherein the quality of the at least one secondary X-ray image is established by a specified amount above the specified threshold value, and the second neural network is trained with respect to ascertaining the characterizing properties using the at least one secondary X-ray image.

4. The method of claim 3, wherein training the first neural network, the second neural network, or the first neural network and the second neural network is initiated by additional primary X-ray images of specified minimum quality as a function of defined criteria.

5. The method of claim 4, wherein the specified criterion is defined as an established duration, a change in an acquisition method of the at least one secondary X-ray image, a detected movement in the at least one secondary X-ray image, a consistency between the generated at least one synthetic X-ray image and the associated secondary X-ray image, a signal relating to a newly identified object in the at least one secondary X-ray image, or any combination thereof.

6. The method of claim 1, wherein the second neural network is trained using the at least one secondary X-ray image, using a secondary X-ray image derived from the at least one primary X-ray image, or using the at least one secondary X-ray image and the secondary X-ray image derived from the at least one primary X-ray image to identify the characterizing properties,
wherein for obtaining the derived secondary X-ray images, the at least one primary X-ray image is reduced in a targeted manner with regard to the respective quality, and wherein the method further comprises aligning or comparing characterizing properties from the at least one primary X-ray image with characterizing properties from the associated derived secondary X-ray image.

7. The method of claim 1, wherein for each generated synthetic X-ray image of the at least one generated synthetic X-ray image, a separate quality criterion is ascertained, and as a function of the respective quality criterion, the first neural network is trained by additional primary X-ray images of specified minimum quality and by secondary X-ray images derived from the additional primary X-ray images,
wherein ascertaining, by the second neural network, the characterizing properties comprises ascertaining, by the second neural network, the characterizing properties from the derived secondary X-ray images, and
wherein the method further comprises providing the characterizing properties to the first neural network for training.

8. The method of claim 1, wherein the characterizing properties are first characterizing properties, and
wherein the method further comprises:
for training, ascertaining, by the second neural network, second characterizing properties using at least one additional primary X-ray image;
providing the second characterizing properties to the first neural network;
generating, by the first neural network, an additional synthetic X-ray image using the provided second characterizing properties; and
comparing, aligning, or comparing and aligning the additional synthetic X-ray image with the at least one additional primary X-ray image.

9. The method of claim 1, further comprising:
transferring the ascertained characterizing properties by a first data channel having a first latency; and transferring the primary X-ray images having the specified minimum quality, information derived from the primary X-ray images, the first neural network, or any combination thereof by a second data channel having a second latency to an external control unit for an external implementation of the method, the second latency being lower than the first latency, wherein the second latency is between 10 and 100 ms.

10. The method of claim 1, further comprising in the case of the at least one secondary X-ray image, establishing a first region and a second region, wherein, compared to the first region, a quality in the second region is at least partially lower and is increased by the first neural network.

11. The method of claim 10, further comprising reducing the quality in the second region by a beam filter, increasing the quality solely in the second region by the first neural network, or a combination thereof.

12. The method of claim 1, further comprising:

respectively detecting the associated characterizing properties by the second neural network using a plurality of secondary X-ray images; and parameterizing, by the first neural network, a movement of the characterizing properties, regions of the secondary X-ray images adjoining the characterizing properties, or a combination thereof.

13. The method of claim 1, further comprising for the providing of the first neural network, training the first neural network, or a combination thereof, providing further primary images from a second modality different than radiography as a first modality, wherein each image of the primary X-ray images and the further primary images is assigned to one modality of the first modality and the second modality.

14. The method of 13, wherein the second neural network is trained using secondary X-ray images from the first modality and secondary images from the second modality.

15. The method of claim 13, further comprising:

obtaining a first portion of the characterizing properties from the at least one secondary X-ray image of the first modality and a second portion of the characterizing properties from the secondary images of the second modality by the second neural network; and generating, by the first neural network, at least one new synthetic X-ray image using a totality of the characterizing properties from the first portion and second portion.

16. The method of claim 15, wherein the quality of the at least one secondary X-ray image is reduced, and based on ascertained quality criterion relating to the generated at least one synthetic X-ray image, the first neural network is trained as a function of the quality criterion using additional primary X-ray images from the first modality, additional primary images from the second modality, or a combination thereof with specified minimum quality, respectively.

17. A control unit for generating synthetic X-ray images, the control unit comprising:

a first neural network that includes two generative adversarial subnetworks and is configured to generate at least one synthetic X-ray image of specified quality; and a second neural network that is configured to:

ascertain characterizing properties from at least one secondary X-ray image; and provide the characterizing properties to the first neural network, wherein the first neural network and the second neural network are trainable using primary X-ray images each having a specified minimum quality, the at least one secondary X-ray image having a lower quality compared to the primary X-ray images, wherein the first neural network is configured to:

generate the at least one synthetic X-ray image using the characterizing properties provided by the second neural network, the at least one synthetic X-ray image being improved with regard to quality compared to the at least one secondary X-ray image.

18. The control unit of claim 17, wherein the second neural network is further configured to ascertain vertebra, fingers, joints, hips, a liver, a pelvis, or any combination thereof as characterizing properties from the at least one secondary X-ray image.

19. A non-transitory computer-readable storage medium that stores instructions executable by a control unit to generate synthetic X-ray images, the instructions comprising:

providing a trained first neural network for generating at least one synthetic X-ray image of specified quality, and a trained second neural network for providing characterizing properties from at least one secondary X-ray image for the first neural network, wherein the first neural network and the second neural network are trainable by primary X-ray images each having a specified minimum quality;

ascertaining the characterizing properties using the at least one secondary X-ray image that has a lower quality compared to the primary X-ray images, by the second neural network; and generating the at least one synthetic X-ray image by the first neural network using the characterizing properties provided by the second neural network, the at least one synthetic X-ray image being improved with respect to quality compared to the at least one secondary X-ray image.

* * * * *